United States Patent
Kimchi et al.

(10) Patent No.: US 6,360,123 B1
(45) Date of Patent: Mar. 19, 2002

(54) APPARATUS AND METHOD FOR DETERMINING A MECHANICAL PROPERTY OF AN ORGAN OR BODY CAVITY BY IMPEDANCE DETERMINATION

(75) Inventors: Yoav Kimchi, Haifa (IL); David Prutchi, Lake Jackson, TX (US); Itzhak Shemer, Haifa (IL)

(73) Assignee: Impulse Dynamics N.V., Curacao (NL)

( * ) Notice: Subject to any disclaimer, the term of this patent is extended or adjusted under 35 U.S.C. 154(b) by 0 days.

(21) Appl. No.: 09/382,269

(22) Filed: Aug. 24, 1999

(51) Int. Cl.[7] ................................................. A61B 5/05
(52) U.S. Cl. ........................ 600/547; 600/588; 324/600; 324/605; 324/606; 324/609; 324/691; 324/692
(58) Field of Search ................................ 600/372, 373, 600/380, 398, 399, 407, 482, 487, 485, 486, 588, 500, 502, 504, 505, 506, 523, 547, 443; 324/602–727

(56) References Cited

U.S. PATENT DOCUMENTS

| | | | |
|---|---|---|---|
| 4,554,922 A | | 11/1985 | Prystowsky et al. |
| 4,559,947 A | | 12/1985 | Renger et al. |
| 4,566,456 A | * | 1/1986 | Koning et al. ............... 607/23 |
| 4,686,987 A | | 8/1987 | Salo et al. |
| 4,702,253 A | | 10/1987 | Nappholz et al. |
| 4,773,401 A | | 9/1988 | Citak et al. |
| 4,901,725 A | | 2/1990 | Nappholz et al. |
| 4,971,058 A | | 11/1990 | Pless et al. |
| 5,003,976 A | * | 4/1991 | Alt ............................... 607/18 |
| 5,083,564 A | | 1/1992 | Scherlag |
| 5,129,394 A | * | 7/1992 | Mehra ......................... 607/23 |
| 5,154,171 A | | 10/1992 | Chirife |
| 5,154,501 A | | 10/1992 | Svenson et al. |
| 5,172,699 A | | 12/1992 | Svenson et al. |
| 5,184,620 A | | 2/1993 | Cudahy et al. |
| 5,197,467 A | | 3/1993 | Steinhaus et al. |
| 5,235,976 A | | 8/1993 | Spinelli |
| 5,281,219 A | | 1/1994 | Kallok |

(List continued on next page.)

OTHER PUBLICATIONS

Hoekstein, KN and Inbar, GF, "Cardiac Stroke Volume Estimation from Two Electrodes Electrical Impedance Measurements", Technion Department of Electrical Engineering Publication EE PUB No. 911, Feb. 1994.

H. Antoni, et al., Polarization Effects of Sinusoidal 50–Cycle Alternating Current on Membrane Potential of Mammalian Cardiac Fibres, Pflugers Arch. 314, pp. 274–291 (1970).

Primary Examiner—Marvin M. Lateef
Assistant Examiner—Jeoyuh Lin
(74) Attorney, Agent, or Firm—Cowan, Liebowitz & Latman, P.C.; William H. Dippert

(57) ABSTRACT

Apparatus and method for determining a mechanical property of an organ or a body part. The method includes positioning an impedance sensor within a blood vessel. The impedance sensor has at least two electrodes disposed within the blood vessel, which is mechanically coupled to the organ or body part. The method further includes determining the electrical impedance between the two electrodes to obtain an impedance signal correlated with the mechanical property of the organ or body part. The organ may be the heart, lungs, uterus, urinary bladder, part of the gastrointestinal tract and the brain. The impedance sensor includes at least two spaced apart electrodes capable of being disposed within a blood vessel. The sensor is operatively connected to an impedance determining unit which determines the impedance between the electrodes. The impedance sensor may be a part of an insertable or implantable lead or catheter like device. Alternatively, the impedance sensor may be a small device adapted to be permanently implanted in a blood vessel and to wirelessly communicate with an external device for transmitting impedance data thereto.

9 Claims, 6 Drawing Sheets

U.S. PATENT DOCUMENTS

| | | | |
|---|---|---|---|
| 5,305,745 A | * 4/1994 | Zacouto | 128/637 |
| 5,353,800 A | 10/1994 | Pohndorf et al. | |
| 5,368,040 A | * 11/1994 | Carney | 128/700 |
| 5,443,489 A | 8/1995 | Ben-Haim | |
| 5,476,484 A | * 12/1995 | Hedberg | 607/23 |
| 5,507,785 A | 4/1996 | Deno | |
| 5,531,772 A | 7/1996 | Prutchi | |
| 5,549,646 A | 8/1996 | Katz et al. | |
| 5,578,064 A | 11/1996 | Prutchi | |
| 5,735,883 A | 4/1998 | Paul et al. | |
| 5,871,506 A | 2/1999 | Mower | |

\* cited by examiner

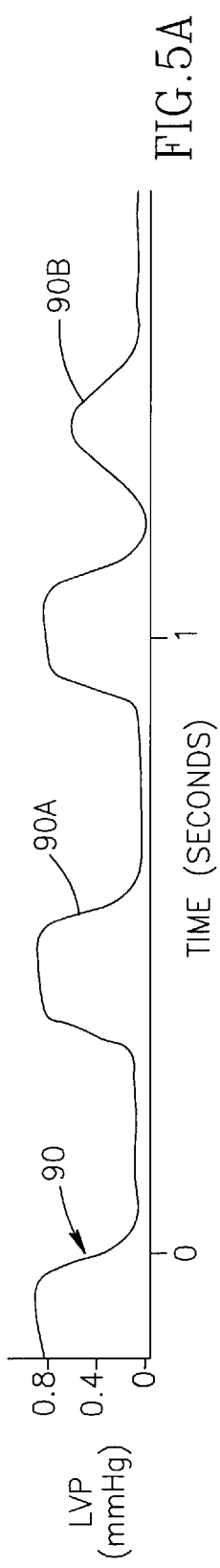
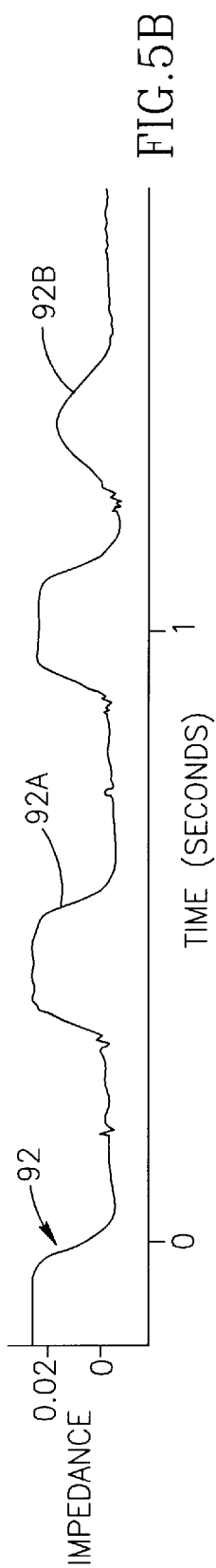
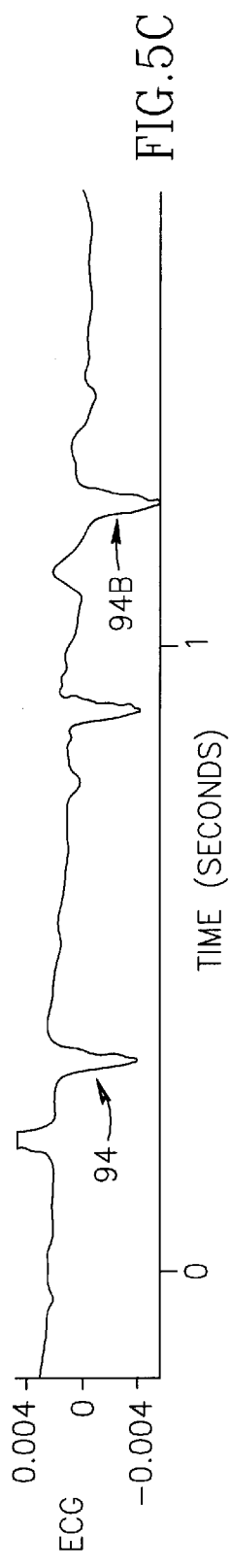
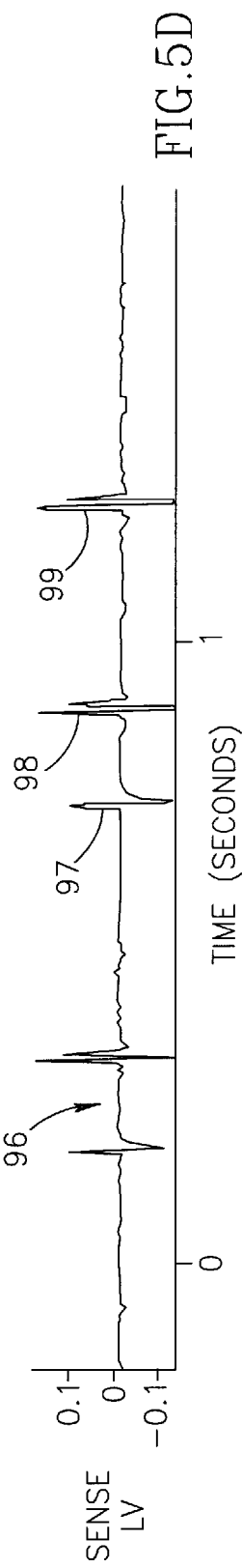

APPARATUS AND METHOD FOR DETERMINING A MECHANICAL PROPERTY OF AN ORGAN OR BODY CAVITY BY IMPEDANCE DETERMINATION

FIELD OF THE INVENTION

The present invention relates generally to the field of impedance determination in biological tissues and more specifically to methods and devices for performing impedance measurements using an impedance sensor having a pair of electrodes which are positioned within a blood vessel.

BACKGROUND OF THE INVENTION

The use of impedance measurements of body tissues or organs for obtaining various mechanical properties and physiological parameters of different organs or body parts are well known in the art. K N Hoekstein and G F Inbar, in a paper titled "Cardiac Stroke Volume Estimation from Two Electrodes Electrical Impedance Measurements" published as Technion Department of Electrical Engineering Publication EE PUB No. 911, February 1994, disclose, inter alia, the use of a two electrode based impedance measurement method and device for estimating cardiac stroke volume of.

Various other applications of Intracardiac impedance methods for measurement of various hemodynamic parameters are well know in the art. Measurement of intracardiac and transcardiac impedance has been described for use in the control of pacemakers and defibrillators. It is commonly accepted that the impedance signal derived from electrodes attached to the heart holds information regarding the cardiac hemodynamics of the patient.

Salo et al., in U.S. Pat. No. 4,686,987 assume that the amplitude of the impedance signal detected through a tripolar lead implanted in the right ventricle (RV) correlates with the heart's stroke volume.

Chirife, in U.S. Pat. No. 5,154,171 has proposed that intracardiac impedance is representative of the volume of the heart and therefore, ejection fraction may be estimated by assuming that the impedance at end-diastole is representative of end-diastolic volume, and the impedance at end-systole is representative of end-systolic volume.

Impedance measurements have also been used to estimate respiratory minute ventilation. For example, U.S. Pat. 4,702,253 to Nappholz et al. discloses a metabolic demand pacemaker utilizing tripolar leads implanted in the right ventricle (RV), or the left atrium for determining the respiratory minute volume by measuring the impedance between a lead electrode and the pacemaker case.

U.S. Pat. No. 4,901,725 to Nappholz et.al disclose a minute volume rate responsive pacemaker utilizing a bipolar lead implanted in the right ventricle for determining the respiratory minute volume by measuring the impedance between a lead electrode and the pacemaker case. The impedance methods disclosed hereinabove by Nappholz et al. have the disadvantage of being sensitive to patient postural changes and to patient activity because of variations in the distance and impedance between the lead electrode and the case due to the posture changes or the patient's activity, respectively.

U.S. Pat. No. 4,773,401 to Citak et al., discloses a quadrupolar electrode implanted in the right ventricle for determining pre-ejection interval to control the rate of a pacemaker.

U.S. Pat. No. 5,235,976 to Spinelli discloses a method and apparatus for managing and monitoring cardiac rhythm using intra-ventricular impedance measurements.

U.S. Pat. No. 5,197,467 to Steinhaus et al., discloses a multiple parameter rate responsive cardiac stimulation apparatus using impedance measurement methods.

U.S. Pat. No. 5,531,772 to Prutchi, U.S. Pat. No. 5,735,883 to Paul et al., and U.S. Pat. No. 5,507,785 to Deno, disclose pacemakers incorporating improved circuitry for cardiac impedance determination for eliminating various types of background interference using various combinations of standard ventricular and/or atrial leads.

U.S. Pat. No. 5,578,064 to Prutchi, discloses a rate responsive cardiac pacemaker with impedance sensing, having impedance measuring circuits using a Wein bridge for eliminating baseline impedance.

A known problem encountered in impedance measurements is that measuring the impedance over a relatively long path results with an impedance signal which is only partially correlated to the mechanical property or to the physiological parameter which one seeks to determine. Additionally, the resulting impedance signal may include signal components which are unrelated to the mechanical property or the physiological parameter which one desires to determine. Such signal components may be due to, inter alia, patient's postural changes, patient's physical activity, or other different physiological parameters or mechanical properties unrelated to the property or parameter that needs to be determined.

Prior art impedance measurements rely on relatively large changes in impedance by using electrodes that are separated widely apart from each other. The advantages of placing the electrodes far apart is that relatively large changes in impedance are measured between the electrodes. This allows a relatively simple circuit to be employed (such as described by Hoekstein and Inbar) which gives relatively large sensitivity of the measured parameter. For example, Hoekstein and Inbar disclose an electrode separation of 2.5 centimeters for measuring right ventricular volume.

Thus, prior art methods suffer from artifacts that are related to posture and movements. This is due to the fact that when widely separated electrodes are used, changes in the distance between the electrodes which are related to posture changes and movements are strongly reflected in the impedance measurement. This effect introduces noise over the desired measured parameter which greatly limits the application of these measurements. Even in the case of two relatively close electrodes of a lead disposed in the right ventricle, there still is the problem of posture or movement since the lead which includes the electrodes bends during movements and causes posture or movement related changes of the measured impedance

SUMMARY OF THE INVENTION

The present invention provides an improved impedance measurement method and device for providing an impedance signal correlated to a mechanical or physiological property of an organ or a part of a body.

The impedance measurement device includes an impedance sensor and an impedance determining unit suitably connected thereto.

A feature of the impedance sensor is that it includes two or more electrodes for impedance determination and that all of the electrodes are disposed within a blood vessel which is mechanically or physically coupled to the organ or the part of the body. The sensor is positioned in the blood vessel such all of the electrodes used for determining the impedance are disposed within the blood vessel. The intra-vessel impedance measured by the device is correlated to the mechanical or physiological property of the organ or the part of a body to which the blood vessel is mechanically or physically coupled.

The impedance measuring unit and the impedance sensor may be adapted for using various impedance measuring methods known in the art, including, but not limited to impedance determining methods using high frequency modulated currents or current pulses, and methods using various test current pulses.

The number of the electrodes included in the impedance sensor may vary depending on the specific impedance measuring method used. An electrode pair configuration is suitable for use in methods which apply, a modulated current or a current pulse or any other current waveform between two electrodes and senses the voltage developed across the same two electrodes. However, more than one electrode pairs can be used.

Alternatively, two electrode pairs may be used in the sensor, a first pair of electrodes for applying a modulated current or a current pulse or any other current waveform therebetween, and a second pair of electrodes for sensing the voltage difference due to the current applied through the first pair of electrodes. However, all the electrodes of the two pairs of electrodes are disposed within the blood vessel. The application of the current to the first pair of electrodes and the measurment of the voltage difference across the second pair of electrodes are performed by the impedance determining unit.

BRIEF DESCRIPTION OF THE DRAWINGS

The invention is herein described, by way of example only, with reference to the accompanying drawings, in which like components are designated by like reference numerals, wherein:

FIGS. 5A–5D are graphs illustrating the results of an in vivo experiment performed in a dog using the impedance determining method of the present invention, for determining an impedance signal correlated with the cardiac left ventricular pressure (LVP)

DETAILED DESCRIPTION OF THE INVENTION

Figure 1:
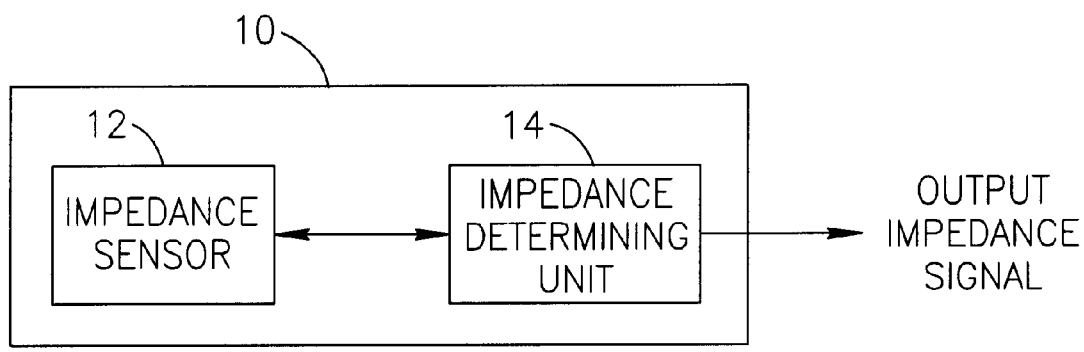
FIG. 1 which is schematic functional block diagram illustrating a device for determining a mechanical property of an organ or body part, using an intra-vessel impedance sensor, in accordance with a preferred embodiment of the present invention.

DETAILED DESCRIPTION OF THE INVENTION
The following terms are used throughout the application:

| Term | Definition |
| --- | --- |
| AICD | Automatic Internal Cardiac Defibrillator |
| CS | Coronary Sinus |
| EMD | Electro-Mechanical Disassociation |
| ETC | Excitable Tissue Control |
| GCV | Great Cardiac Vein |
| LV | Left Ventricle |
| LVP | Left Ventricular Pressure |
| PVC | Premature Ventricular Contraction |
| RV | Right Ventricle |
| SVC | Superior Vena Cava |
| VF | Ventricular Fibrilation |
| VT | Ventricular Tachicardia |

The present invention discloses a novel method for determining a mechanical property of an organ or body cavity which is capable of undergoing mechanical changes by determining the electrical impedance within a blood vessel which is responsive to the mechanical property of the organ or body cavity. Typically, the organ is a contractile or motile organ which includes muscular tissue, such as but not limited to the heart, the uterus, a part of the gastrointestinal tract, and the like. However, the method and the devices of the present invention may also be applied for determining a mechanical property of an organ which by itself has no muscular or contractile tissues but is mechanically coupled to other organs or muscles or organ combinations or contractile tissues which have contractile or motile properties which influence the mechanical property of the organ coupled thereto. For example, the lungs may change their volume, size, pulmonary pressure and other mechanical properties, in response to contractions and relaxations of the respiratory muscles including , inter alia, intercostal muscles, abdominal muscles and diaphragm muscles which affect the lungs through changes in the volume, pressure and other mechanical properties of the chest volume mediated, inter alia, through pleural coupling. The present invention may be applied to such organs like the lungs. Additionally the method of the present invention may be applied for determining a mechanical property of a body cavity. For example, the present invention may be applied for determining the intra-thoracic pressure by determining the impedance signal of an impedance sensor (not shown) disposed within a branch of the azygos vein which is disposed within the intra-thoracic cavity and is responsive to the intra-thoracic pressure.

The method of the present invention is based on the positioning of a suitable electrical impedance sensor within a blood vessel, such as a vein or an artery which is mechanically responsive to the mechanical property of the organ or body cavity of interest and determining the intra-vessel electrical impedance. The term intra-vessel impedance is used hereinafter to define an impedance measured within a blood vessel by using two or more of electrodes, wherein all of the electrodes used for the impedance measurement are disposed within the blood vessel. This intra-vessel electrical impedance signal is correlated to the mechanical property of the organ or cavity, such as, but not limited to, the pressure within a fluid containing body cavity or of a compartment or cavity disposed within the organ, the amplitude of the mechanical contraction of the organ or a part thereof or other mechanical properties of the organ or a part thereof.

Reference is now made to FIG. 1 which is schematic diagram illustrating a device for determining a mechanical property of an organ, using an intra-vessel impedance sensor, in accordance with a preferred embodiment of the present invention.

The device 10 includes an intra-vessel impedance sensor 12, operatively connected to an impedance determining unit 14. The impedance determining unit 14 determines the intra-vessel impedance as sensed by the sensor 12 which is adapted to be disposed within a blood vessel (not shown in FIG. 1 for the sake of clarity of illustration), using any suitable method for electrical impedance measurement known in the art, as is disclosed in detail hereinafter. The output impedance signal may be used or monitored by suitably connecting the device 10 to another separate device (not shown) for further processing, or display. Alternatively, the device 10 may be integrated within another device, such as, but not limited to a cardiac pacemaker (not shown), a defibrillator (not shown), a cardiac contractility modulating device (not shown), a smooth muscle controller device (not shown), or within any other device adapted to process or make use of an impedance signal correlated to a mechanical property of the organ which is mechanically coupled to the blood vessel within which the impedance sensor 12 is disposed or implanted.

Figure 2:
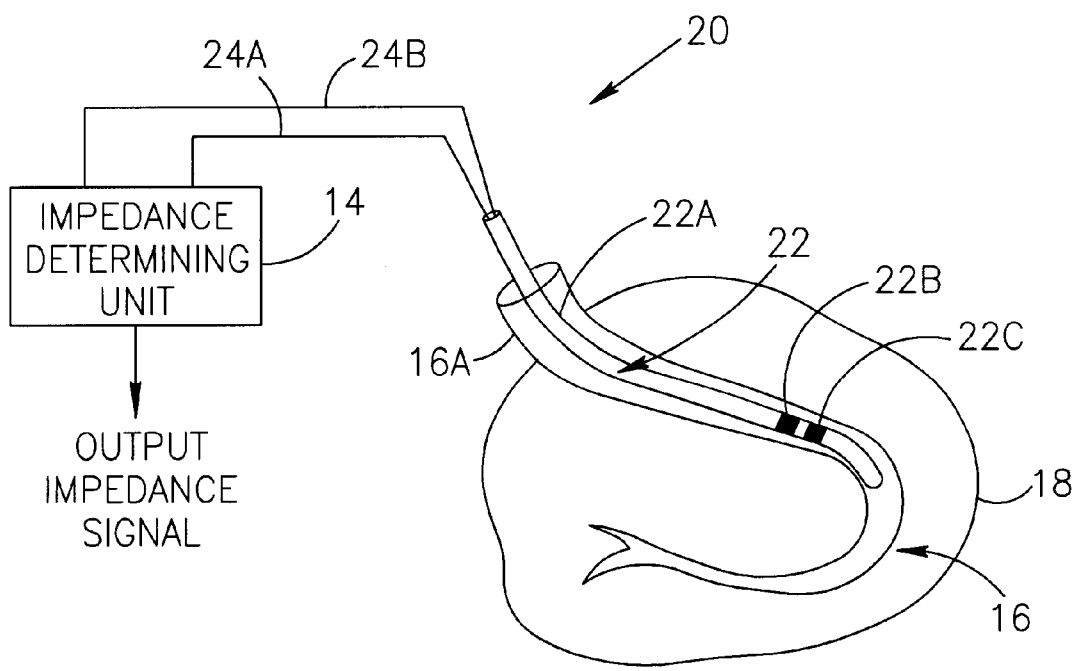
FIG. 2 is a schematic diagram illustrating a device for determining a mechanical property of an organ having an impedance sensor disposed in a blood vessel coupled to an organ, in accordance with a preferred embodiment of the present invention.

Reference is now made to FIG. 2 which is a schematic diagram illustrating a device 20 for determining a mechanical property of an organ having an impedance sensor disposed in a blood vessel coupled to an organ, in accordance with a preferred embodiment of the present invention.

The device 20 includes the impedance determining unit 14 of FIG. 1 operatively connected to an intra-vessel impedance sensor 22. The impedance sensor 22 includes a lead 22A and two electrodes 22B and 22C spaced apart along the lead 22A. The electrodes 22B and 22C are electrically isolated from each other and are electrically connected to the impedance determining unit 14 by suitable electrically isolated conductors 24A and 24B disposed within the lead 22A.

The lead 22A of the sensor 22 is disposed within the lumen of a blood vessel 16. The blood vessel 16 is mechanically coupled to an organ 18. The blood vessel 16 may be a blood vessel such as a vein or an artery embedded within the organ 18 and supplying blood to the organ 18. However, the blood vessel 16 may also be a blood vessel which is physically coupled or mechanically coupled to the organ 18 but not embedded within the organ 18. A feature of the method of the present invention is that the vessel walls 16A of the blood vessel 16 or a portion of the vessel walls 16A are responsive to the mechanical property which is to be determined, as is disclosed in detail hereinafter. In accordance with one non-limiting example of the present invention, the organ 18 is the heart, the blood vessel 16 is a lateral branch of the great cardiac vein (GCV). The mechanical property which is determined by measuring the intra-vessel impedance is the left ventricular pressure (LVP). When the sensor 22 is disposed within a branch of the GCV, the impedance signal which is output by the impedance determining unit 14 is highly correlated to the LVP as is shown in detail hereinafter.

An important feature of the impedance sensing method and impedance sensors of the present invention is that the electrodes used for determining the intra-vessel impedance, such as, for example, the pair of electrodes 22B and 22C of the sensor 22, are both disposed within the lumen of the blood vessel. Generally, one of the electrodes of the pair functions as a current source and the other electrode of the pair functions as a current sink, the current source electrode and the current sink electrode are disposed within the lumen of the blood vessel. Preferably, the impedance is determined by determining the voltage difference across the same pair of electrodes 22B and 22C. This has the advantage of reducing the number of electrodes and electrical conductors in the lead 22A and the sensor 22. However, in accordance with another embodiment of the present invention, the impedance sensor of the present invention may include two pairs of electrodes (not shown in FIG. 2). One pair of electrodes functions as a current sink and source and the other pair of electrodes senses the voltage difference due to the current flow.

Figure 3:
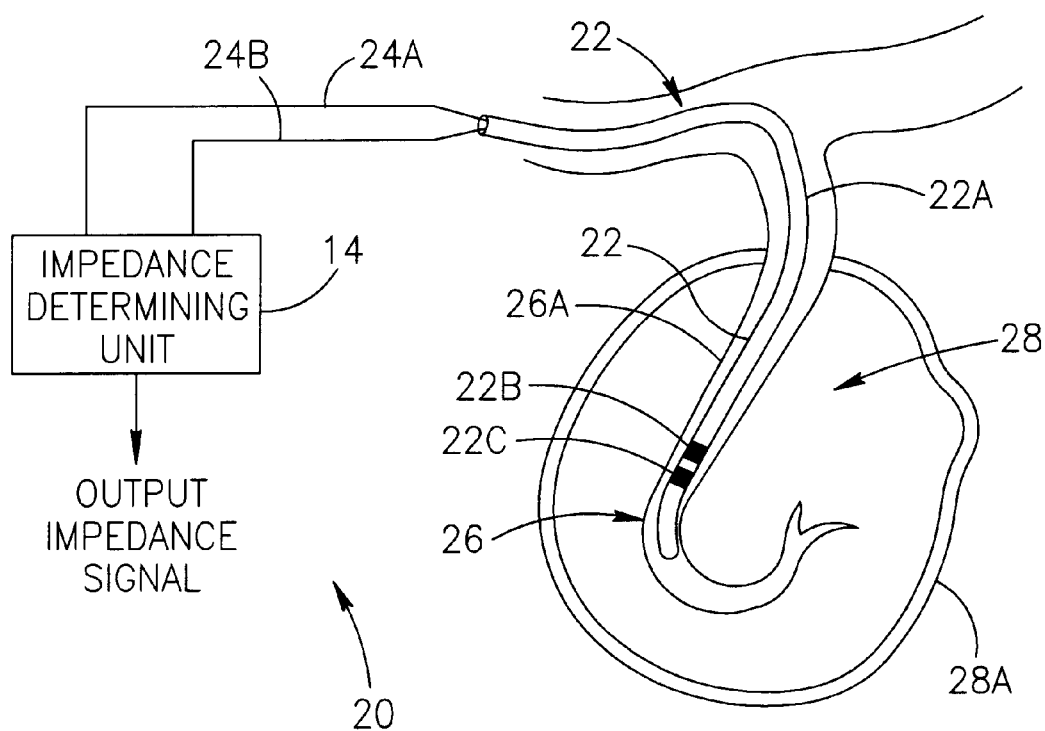
FIG. 3 is a schematic diagram illustrating the impedance sensor of the device 20 of FIG. 2, disposed in a blood vessel which is responsive to a mechanical property within a body cavity or organ cavity in accordance with another preferred embodiment of the present invention.

Reference is now made to FIG. 3 which is a schematic diagram illustrating the impedance sensor of the device 20 of FIG. 2, disposed in a blood vessel which is responsive to a mechanical property within a body cavity in accordance with another preferred embodiment of the present invention.

The device 20 is of FIG. 3 is similar to the device 20 of FIG. 2 except that the sensor 22 of FIG. 3 is disposed in a blood vessel 26 which is disposed within a body cavity 28. The body cavity 28 may be surrounded by a cavity wall 28A. In accordance with one, non-limiting example, the body cavity 28 may be the intra-thoracic cavity and the blood vessel may be a branch of the azygos vein (the lungs and the details of the ribs and intercostal muscles are not shown for clarity of illustration). In such an example, the walls of the azygos vein branch are responsive to the intra-thoracic pressure which is the mechanical property which is correlated to the impedance signal sensed by the sensor 22 However, the cavity 28 may be any other body cavity, provided that the intra-vessel impedance signal of the sensor 22 is correlated with the mechanical property which needs to be determined.

It is noted that the body cavity may be a fluid filled cavity, such as, but not limited to the uterine cavity of the uterus during pregnancy.

It is further noted that the blood vessel 26 may or may not be disposed within the cavity 28. For example, the blood vessel 26 may be embedded within the cavity wall 28A surrounding the cavity 28. In accordance with one non-limiting example, the cavity wall 28A is the uterine wall and the sensor 22 is disposed in the lumen of a uterine vein embedded within or attached to or mechanically coupled to the uterine wall. In such an example the intra-vessel impedance determined by the impedance sensor 22 may be correlated to the intrauterine pressure level, and may be used, inter alia, to monitor uterine contractions. In accordance with another , non-limiting example, the sensor 22 is disposed within a vein attached to or embedded in the urinary bladder and the cavity wall 28 A represents the wall of the urinary bladder. In such an example, the intra-vessel impedance may be correlated to the internal pressure within the bladder or to another bladder related physiological parameter.

It is noted that the impedance sensor of the present invention may be implemented with many different variations in its shape and dimensional characteristics.

Reference is now made to FIGS. 4A–4D which are schematic diagrams illustrating different types of impedance sensor implementations usable with the impedance determining device of FIG. 1.

Figure 4A:
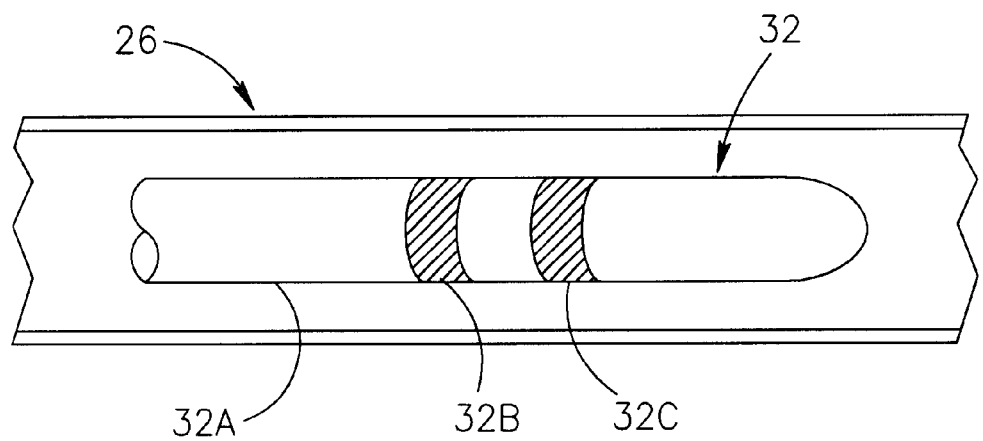
FIGS. 4A–4F are schematic diagrams illustrating different types of impedance sensor implementations usable with the impedance determining device of FIG. 1.

FIG. 4A is an isometric view of part of a sensor 32 disposed within a blood vessel 26 shown in a cross-sectional view. The sensor 32 includes an elongated lead 32A and two electrodes 32B and 32C attached to the lead 32A. The electrodes 32B and 32C are both disposed within the lumen of the blood vessel 26 and are electrically connected to suitable electrically conducting wires (not shown) as is known in the art, for electrically connecting the electrodes to an impedance determining unit (not shown), such as but not limited to the impedance determining unit 14 of FIG. 1. The electrodes 32B and 32C are longitudinally separated along the longitudinal axis (not shown) of the sensor 32. The electrodes 32B and 32C are made of an electrically conducting material which is, preferably bio-compatible, such as, but not limited to platinum, titanium or the like. Typically, but not necessarily, the electrodes 32B and 32C are ring like or are made as an electrically conducting coil wound on the lead 32A which is made from an electrically non-conducting material. Preferably, but not necessarily, the distance separating the electrodes 32B and 32C along the longitudinal axis (not shown) of the sensor 32 is within an order of magnitude of the dimension of the electrodes 32B and 32C along the longitudinal axis of the sensor 32. Typically, in a sensor useful for determining intra-venous impedance within coronary veins of the heart, the dimension of the electrodes 32B and 32C along the longitudinal axis of the sensor 32 are approximately 0.5–1.0 millimeters and the distance between the electrodes 32B and 32C along the longitudinal axis of the sensor 32 is approximately 1–2 millimeters. However, other different dimensions may also be used which may depend, inter alia, on the blood vessel's diameter and/or length, the specific application, and other lead manufacturing considerations. Preferably, but not necessarily, the dimensions and shapes of the electrodes 32B and 32C are similar. However, the dimensions and shapes of the electrodes 32B and 32C may also differ.

It is noted that, while in the sensor 32, the electrodes 32B and 32C are shown as being constructed to be flush with the outer surface of the lead 32A, the electrodes 32B and 32C may also be radially or transversally elevated with respect to the surface of the lead 32A (as happens when the electrodes 32B and 32C are implemented as coils wound on the lead 32A). However, The impedance electrodes may also be radially sunk with respect to the outer surface of the lead 32A.

Figure 4B:
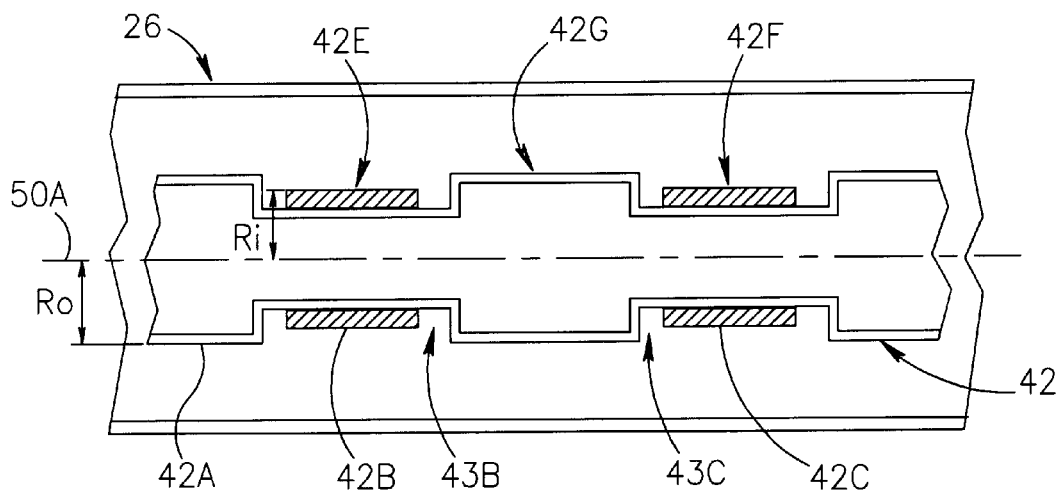

FIG. 4B is a schematic cross sectional view of an impedance sensor 42 having sunk electrodes, in accordance with a preferred embodiment of the present invention. The sensor 42 is similar to the sensor 32, except that the lead 42A has two longitudinally spaced apart recesses 43B and 43C therein, and that the impedance electrodes 42B and 42C are disposed within the recesses 43B and 43C, respectively, such that their outward facing surfaces 42E and 42F, respectively, have a radial distance Ri which is smaller than the radial distance Ro of the external surface 42G of the lead 42A with respect to the longitudinal axis 50A of the sensor 42. The sensor 42 may have the advantage that the recessed electrodes 42B and 42C are prevented from contacting the walls of the blood vessel 26 even if the diameter of the lumen of the blood vessel 26 is similar or close to the outer diameter of the lead 42A and even if the lead 42A is placed in contact with a portion of the wall of the blood vessel 26.

Figure 4C:
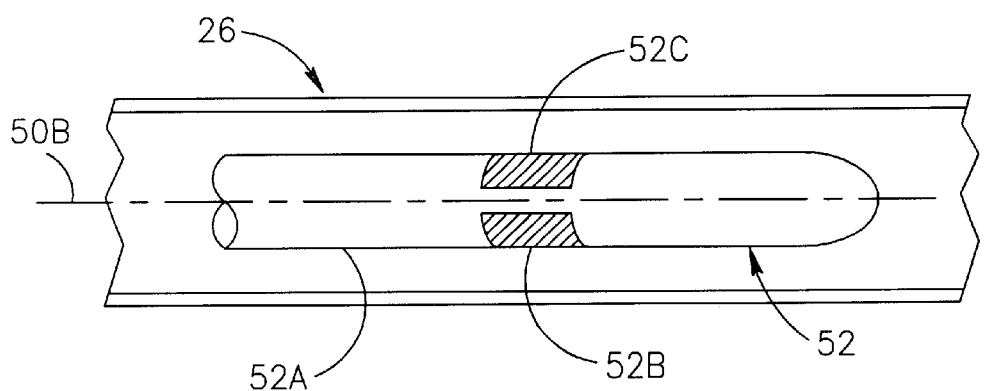

FIG. 4C schematically illustrates an impedance sensor 52. The impedance sensor 52 includes two electrodes 52B and 52C which are attached to a lead 52A. The electrodes 52B and 52C are transversally separated from each other with respect to the longitudinal axis 50B of the sensor 52. The electrodes 52B and 52C may have various shapes, such as, but not limited to, ring segments, circular dots(not shown), rectangular shapes (not shown) or any other suitable shapes.

Figure 4D:
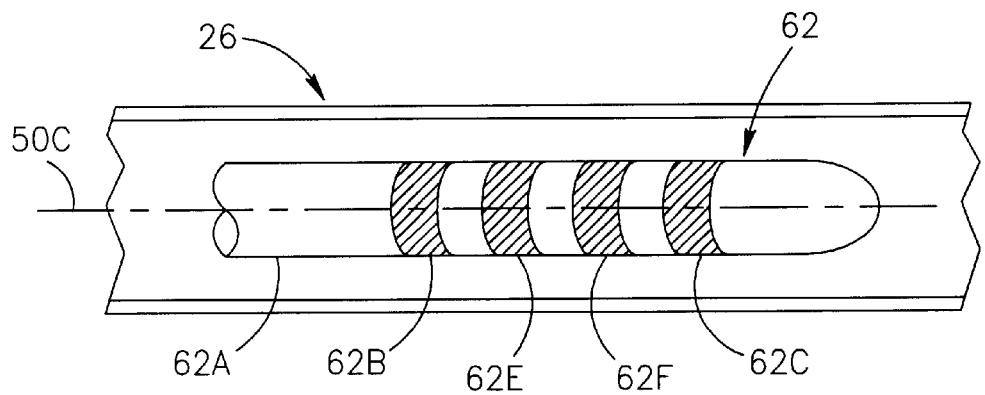

FIG. 4D schematically illustrates an impedance sensor 62. The impedance sensor 62 includes two electrode pairs 62B and 62C, and 62E and 62F. The electrodes 62B, 62C, 62E and 62F are attached to a lead 62A. The electrodes 62B, 62C, 62E and 62F may have various shapes, such as, but not limited to, rings, ring segments, circular dots(not shown), rectangular shapes (not shown) or any other suitable shapes. The electrodes 62B, 62C, 62E and 62F are spaced apart from each other along the longitudinal axis 50C of the sensor 62. The sensor 62 may be used for impedance determination by using the electrodes 62B and 62C as current electrodes and the electrodes 62E and 62F as voltage sensing electrode as is known in the art and disclosed hereinafter. The dimensions and spacing of the electrodes 62B, 62C, 62E and 62F may vary.

It will be appreciated by those skilled in the art that many variations are possible in the geometrical dimensions of the impedance electrodes, their arrangement and separation along the lead, their shapes, sizes and methods of construction. The number of the electrodes may also vary. For example, the lead 62A of FIG. 4D may be a recessed lead having four recesses (not shown) and the four electrodes 62B,62C, 62E and 62F of FIG. 4D may be attached to within those recesses. In another example, the electrodes 52B and 52C of the sensor 52 of FIG. 4C may also be attached to the lead 52A within appropriate recesses (not shown) formed within the lead 52A.

One possible method for determining impedance in a tissue includes passing a high frequency modulated current signal through a pair of electrodes, such as, for example the electrodes 22B and 22C of FIG. 2 and low pass filtering and demodulating the voltage signal which develops across the electrodes 22B and 22C. The impedance may then be obtained by dividing the voltage by the current. Alternatively, the amplitude envelope of the demodulated impedance signal is used as a signal which is correlated to the impedance. For example, the circuits disclosed by Citak in U.S. Pat. No. 4,773,401, the circuits disclosed by Chirife in U.S. Pat. No. 5,154,171, or the circuits disclosed by Spinelli in U.S. Pat. No. 5,235,976 or modifications thereof may be used to implement the impedance determining unit 14 of FIG. 1 of the present invention. High frequency modulated current based impedance measuring devices and methods are known in the art, are not the subject matter of the present invention and are therefore not disclosed in detail hereinafter.

Additional methods and devices for impedance determination which are more resistant to electrical noise and to tissue myo-electric variations or other property variations are known in the art. Such methods provide a correct impedance signal even in the presence of very strong pacing pulses and electromagnetic interference.

For example, the impedance circuits disclosed in U.S. Pat. No. 5,531,772 to Prutchi, the entire specification of which is incorporated herein by reference, may be used in the present invention.

The impedance circuits disclosed in U.S. Pat. No. 5,735,883 to Paul et al., the entire specification of which is incorporated herein by reference, may also be used in the present invention.

The impedance circuits disclosed in U.S. Pat. No. 5,507,785 to Deno et al., the entire specification of which is incorporated herein by reference, may also be used in the present invention.

The impedance circuits disclosed in U.S. Pat. No. 5,578,064 to Prutchi, the entire specification of which is incorporated herein by reference, may also be used in the present invention.

The impedance sensing circuits disclosed by Prutchi, Paul et al., and Deno are well suited for use in the present invention as a possible implementation of the impedance determining unit 14 of FIG. 1. These impedance sensing circuits are capable of measuring the correct impedance value between two electrodes of a pacing system and are effectively immune to electrode polarization effects, electromagnetic interference and other interfering artifacts. However, many other impedance measuring circuits known in the art may be used in implementing the impedance determining unit 14 of FIG. 1 of the present invention.

It is noted that for the sake of clarity of illustration, the electrical conductors connecting the electrodes of FIGS. 2, 3, 4A, 4B, 4C and 4D with the impedance determining unit 14 are not shown.

While the impedance sensors disclosed hereinabove are implemented as an insertable or implantable lead or catheter like elongated device, other different embodiments of the device of the present invention may also be constructed which are within the scope of the invention.

Figure 4E:
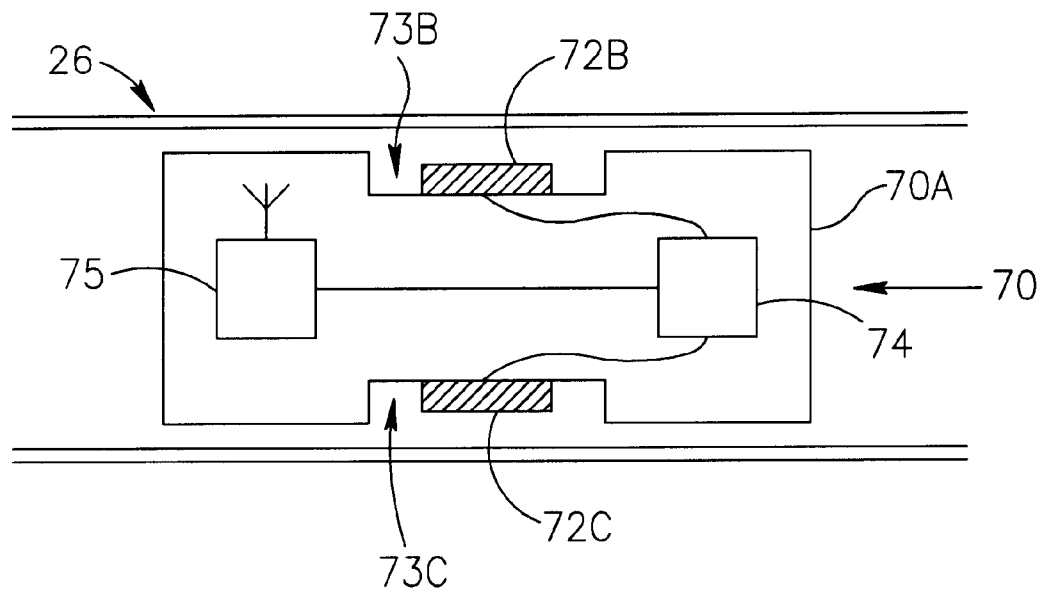
Figure 4F:
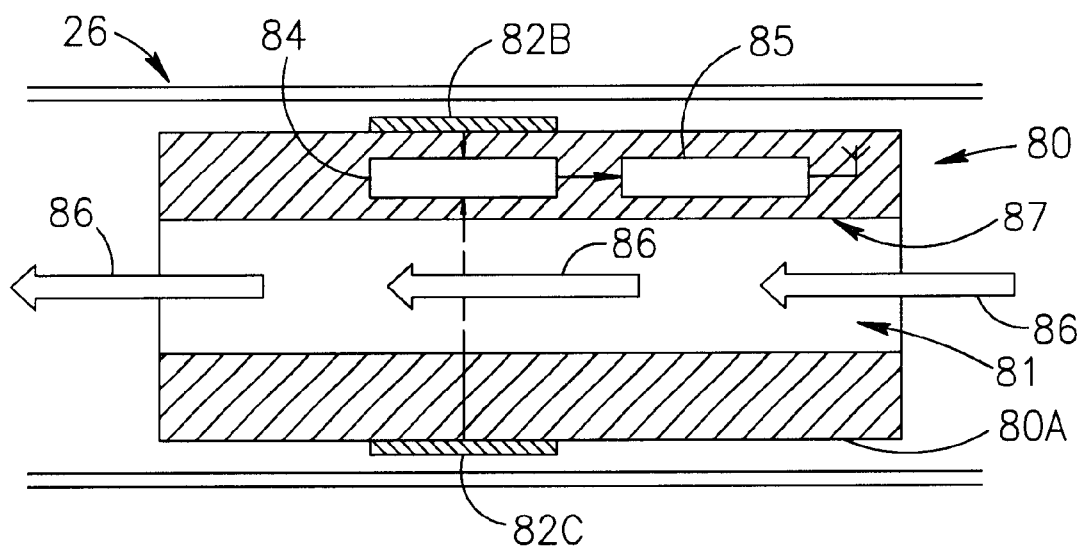

Reference is now made to FIGS. 4E and 4F which are schematic cross-sectional diagrams of implantable impedance measuring devices having telemetry capabilities for determining a mechanical property of an organ, using an intra-vessel impedance sensor, in accordance with a preferred embodiment of the present invention.

FIG. 4E illustrates a implantable impedance measuring device 70. The device 70 includes a cylindrical housing 70A. The housing 70A has recesses 73B and 73C therein. The device 70 includes two impedance electrodes 72B and 72C, attached to the housing 70A within the recesses 73B and 73C, respectively. The device 70 further includes an impedance determining unit 74 encased within the housing 70A. The electrodes 72B and 72C are electrically connected to the impedance determining unit 74. The impedance determining unit 74 may be any suitably sized or miniaturized implementation or version of any of the circuits disclosed hereinabove or known in the art which are suitable for measuring impedance as disclosed hereinabove.

The device 70 also includes a telemetry unit 75 for receiving impedance signals from the impedance determining unit 74 and telemetrically transmitting an analog or digital signal representing the received impedance signal to a suitable telemetry receiver or transceiver. In accordance with one preferred embodiment of the invention, the device 70 includes a power source (not shown) disposed within the housing 70A such as a battery or the like for energizing the impedance determining unit 74 and the telemetry unit 75. In accordance with another preferred embodiment of the invention, the device 70 may include a power receiving and storing device (not shown) which may wirelessly receive power from a power source external to the device 70 or to the body of the patient in which the device 70 is implanted. The wireless power transmission may be implemented using electromagnetic waves, ultrasound or sound waves or any other wireless power transmitting method known in the art. The wirelessly transmitted power may be stored in a rechargeable cell (not shown) or in any other suitable power storage (not shown) or power conversion and storage device (not shown) known in the art.

In operation, the device 70 is inserted into a suitable blood vessel 26 of the patient which is mechanically coupled to an organ or body part of the patient and disposed within the blood vessel. The device 70 may then be used (after telemetrical activation thereof if implemented) to determine the intra-vessel impedance by using the electrodes 72B and 72C as disclosed for the impedance sensors disclosed hereinabove. The impedance signal or the data representing it may then be transmitted to an appropriate receiving device (not shown) outside the patient's body for further processing or for determining the mechanical property or physiological parameter which is correlated to the measured impedance as disclosed hereinabove.

It will be appreciated that, while the embodiment of the device 70 of FIG. 4E illustrates a cylinder shaped recessed device having a single pair of impedance measuring electrodes, the implantable impedance determining device of the present invention may be differently shaped and may be implemented with other different numbers of electrodes or electrode pairs. For example the device 70 may be adapted to include two electrode pairs suitably arranged for measuring intra-vessel impedance as disclosed hereinabove for the impedance sensor 42 of FIG. 4D, in accordance with another non limiting example, the arrangement of the electrodes 72B and 72C may be modified to be similar to the relative arrangement of the electrodes 32B and 32C of the impedance sensor 32 of FIG. 4A.

In cases in which it is desired not to interrupt or excessively reduce the flow of blood through the blood vessel 26 within which the impedance determining device is implanted the design of the device may be modified by including a hollow passage therein.

FIG. 4F illustrates a hollow implantable impedance measuring device 80. The device 80 includes a hollow cylindrical housing 80A. The device 80 includes two impedance electrodes 82B and 82C, attached to the housing 80A. The device 80 further includes an impedance determining unit 84 encased within the housing 80A. The electrodes 82B and 82C are electrically connected to the impedance determining unit 84. The impedance determining unit 84 may be any suitably sized or miniaturized implementation or version of any of the circuits disclosed hereinabove or known in the art which are suitable for measuring impedance as disclosed hereinabove.

The device 80 also includes a telemetry unit 85 for receiving impedance signals from the impedance determining unit 84 and telemetrically transmitting an analog or digital signal representing the received impedance signal to a suitable telemetry receiver or transceiver. In accordance with one preferred embodiment of the invention, the device 80 includes a power source (not shown) disposed within the housing 80A such as a battery or the like for energizing the impedance determining unit 84 and the telemetry unit 85. In accordance with another preferred embodiment of the invention, the device 80 may include a power receiving and storing device (not shown) which may wirelessly receive power from a power source external to the device 80 or to the body of the patient in which the device 80 is implanted. The wireless power transmission may be implemented using electromagnetic waves, ultrasound or sound waves or any other wireless power transmitting method known in the art. The wirelessly transmitted power may be stored in a rechargeable cell (not shown) or in any other suitable power storage (not shown) or power conversion and storage device (not shown) known in the art.

The device 80 is a hollow device, and has a passage or hole 81 passing therethrough.

In operation, the device is 80 inserted into a suitable blood vessel 26 of the patient which is mechanically coupled to an organ or body part of the patient and disposed within the blood vessel. The blood flow within the blood vessel 26 may continue after implantation as the blood may flow through the hollow passage 81. For example, the direction of the blood flow through the passage 81 is indicated by the arrows 86. It is noted that the direction of the blood flow through the passage 81 may depend on the device's orientation within the blood vessel 26 and on the direction of blood flow before the device 80 was implanted within the blood vessel 26.

The device 80 may then be used (after telemetrical activation thereof if implemented) to determine the intra-vessel impedance by using the electrodes 82B and 82C as disclosed for the impedance sensors disclosed hereinabove. The impedance signal or the data representing it may then be transmitted to an appropriate receiving device (not shown) outside the patient's body for further processing or for determining the mechanical property or physiological parameter which is correlated to the measured impedance as disclosed hereinabove.

The device 80 may be advantageously used in cases where it is preferred to implant the device 80 within an artery, since it decreases the degree of blood flow reduction due to implantation of the device and allows arterial blood to reach its destination.

It will be appreciated that, while the embodiment of the hollow device 80 of FIG. 4F illustrates a hollow cylinder shaped device having a single pair of impedance measuring electrodes, other preferred embodiments of hollow implantable impedance determining devices of the present invention may be differently shaped and may be implemented with other different numbers of electrodes or electrode pairs. For example the device 80 may be adapted to include two electrode pairs suitably arranged for measuring intra-vessel impedance as disclosed hereinabove for the impedance sensor 42 of FIG. 4D, in accordance with another non limiting example, the arrangement of the electrodes 82B and 82C may be modified to be similar to the relative arrangement of the electrodes 32B and 32C of the impedance sensor 32 of FIG. 4A. Additionally, the dimensions and shape of the hollow passage 81 may be modified in order to improve the blood flow therethrough. For example, the shape of the passage 81 may deviate from the illustrated shape of a cylindrical passage to improve the hydrodynamic blood flow properties therethrough in order to reduce undesired turbulence. In another example, the inner surface 87 defining the passage 81 may be suitably chemically or physically treated or coated with a suitable material for improving the blood flow therethrough.

It is noted that while the device 80 of FIG. 4F is a hollow device to enable blood flow therethrough, the device 80 may also be formed as a non hollow device (not shown). Moreover, when the device 70 of FIG. 4E or a non-hollow version (not shown) of the device 80 of FIG. 4F is disposed within a vein, it may be positioned such as to completely or almost completely block the flow of blood within the vein. This type of positioning may have the advantage of reducing undesirable movements and displacements of the devices 70 or 80 or the variations thereof and may increase the stability of the impedance measurement. For relatively small veins such blocking is usually not clinically prohibited since other non-blocked veins may provide suficient venous drainage of the organ region or body part. Similarly, the elongated sensors 22, 32, 42, 52 and 62 of FIGS. 3, 4A, 4b, 4C and 4D may be disposed within a vein in such a way as to completely or almost completely block the flow of blood within the vein.

EXAMPLE 1

An in vivo experiment demonstrating the use of the impedance measurement method and device of the present invention was performed. A mongrel dog was anasthesized. A model SPC-751 MIKRO-TIP® Catheter pressure transducer was inserted into the left ventricle through the aortic valve, via the femoral artery and positioned within the left ventricle such that it did not contact the left ventricle walls. The pressure catheter was suitably connected to a model TCB-500 Transducer Control Unit for LVP monitoring. The catheter pressure transducer and the transducer control unit are commercially available from Millar Instruments, Inc. Texas, U.S.A. Standard ECG electrodes were arranged for recording ECG signals. A lead including two closely spaced sensing electrodes at its distal end (not shown) was inserted through the jugular vein the superior vena cava (SCV) and the coronary sinus CS, into the great cardiac vein (GCV). The distal end of the lead was similar in construction to the lead 32A of the impedance sensor 32 of FIG. 4A, except that it further included two additional ETC electrodes (not shown) flanking the sensing electrodes. The sensing electrodes constituted two electrically conducting wires tightly coiled on the outer surface of the lead. The longitudinal dimension of each of the two sensing electrodes along the longitudinal axis of the lead was 1 millimeter and the distance separating the two sensing electrodes along the longitudinal lead axis was 2 millimeters. The two sensing electrodes were simultaneously used for impedance determination and for locally sensing a differential local left ventricular electrogram signal. The sensing electrodes were suitably electrically connected to an external impedance determining unit including an impedance circuit which is a modified version of the impedance determining circuit disclosed as the impedance circuit 42 of FIG. 1 of U.S. Pat. No. 5,531,772 to Prutchi, operating as disclosed in detail by Prutchi. With the exception that the circuit was not a part of a pacemaker and was therefore not connected to a microprocessor as was the circuit 42 of FIG. 1 of U.S. Pat. No. 5,531,772. For the local sensing the two sensing electrodes were also connected to a suitable external differential amplifier (not shown).

The impedance signal thus recorded represented the intravessel impedance determined within the GCV referred to as the GCV impedance signal hereafter. The GCV impedance signal, the locally sensed left ventricular electrogram signal, the LVP signal and the ECG signal were simultaneously recorded stored for further processing and analysis using computerized data acquisition.

Reference is now made to FIGS. 5A–5D which are graphs illustrating the results of the experiment of EXAMPLE 1 performed using the impedance determining method of the present invention, for determining an impedance signal correlated with the cardiac left ventricular pressure (LVP).

The horizontal axis of all the graphs of FIGS. 5A–5D commonly represents the time in seconds. The curve 90 of FIG. 5A represents the experimentally determined cardiac left ventricular pressure as measured by the Millar catheter pressure transducer and the vertical axis of the graph of FIG. 5A represents the left ventricular pressure amplitude in millimeters Hg.

The curve 92 of FIG. 5B represents the experimentally determined GCV impedance signal, as measured by the sensing electrodes of the lead disposed within the GCV and the impedance measuring unit, and the vertical axis of the graph of FIG. 5B represents the GCV impedance signal amplitude in arbitrary units.

The curve 94 of FIG. 5C represents the experimentally determined ECG signal and the vertical axis of the graph of FIG. 5A represents the ECG signal amplitude in arbitrary units.

The curve 96 of FIG. 5D represents the experimentally determined locally sensed left ventricular differential electrogram signal as measured by the differential amplifier connected to the sensing electrodes, and the vertical axis of the graph of FIG. 5D represents the left ventricular electrogram signal amplitude in arbitrary units.

Turning to FIGS. 5A and 5B, it can be seen that the LVP signal curve 90 is highly correlated to the GCV impedance signal curve 92. The part 90A of curve 90 and the part 92A of the curve 92 represent the LVP changes and the GCV impedance changes, respectively, during part of a normal cardiac beat cycle.

The part 90B of curve 90 and the part 92B of the curve 92 represent the LVP changes and the GCV impedance changes, respectively, during a premature ventricular beat (PVC) which spontaneously occurred in the dogs heart during the experiment. It can be seen that the PVC related LVP signal 90B is highly correlated to the PVC related GCV impedance signal 92B.

Turning to FIG. 5C, the curve part 94B represents an early depolarization in the ECG curve 94. This early depolarization is associated with the PVC represented by the curve parts 90B and 92B of FIGS. 5A and 5B, respectively.

Turning to FIG. 5D, the differential left ventricular electrogram curve 96 illustrates electrical sensed events associated with normal beats and with the PVC. In a normal cardiac beat, the differential electrogram has an early component 97 which is associated with the right atrial depolarization wave and a later component 98 which is associated with the left ventricular depolarization wave. It is noted that the PVC represented by the curve parts 90B and 92B of FIGS. 5A and 5B, respectively is preceded by an event 99 on the left ventricular electrogram curve 96, which represents the activation of the left ventricle only and is not associated by an earlier event related to an atrial activation.

To quantitatively determine the correlation between the experimentally determined LVP signal and the experimentally determined GCV impedance signal, the LVP curve 90 and the GCV impedance curve 92 were sampled at 500 equally spaced time points of an arbitrarily selected normal beat cycle similar (but not identical) to the curve parts 90A and 92A, to yield two sets of 500 data points. The correlation coefficient r of these two data sets was r=0.992.

Figure 6:
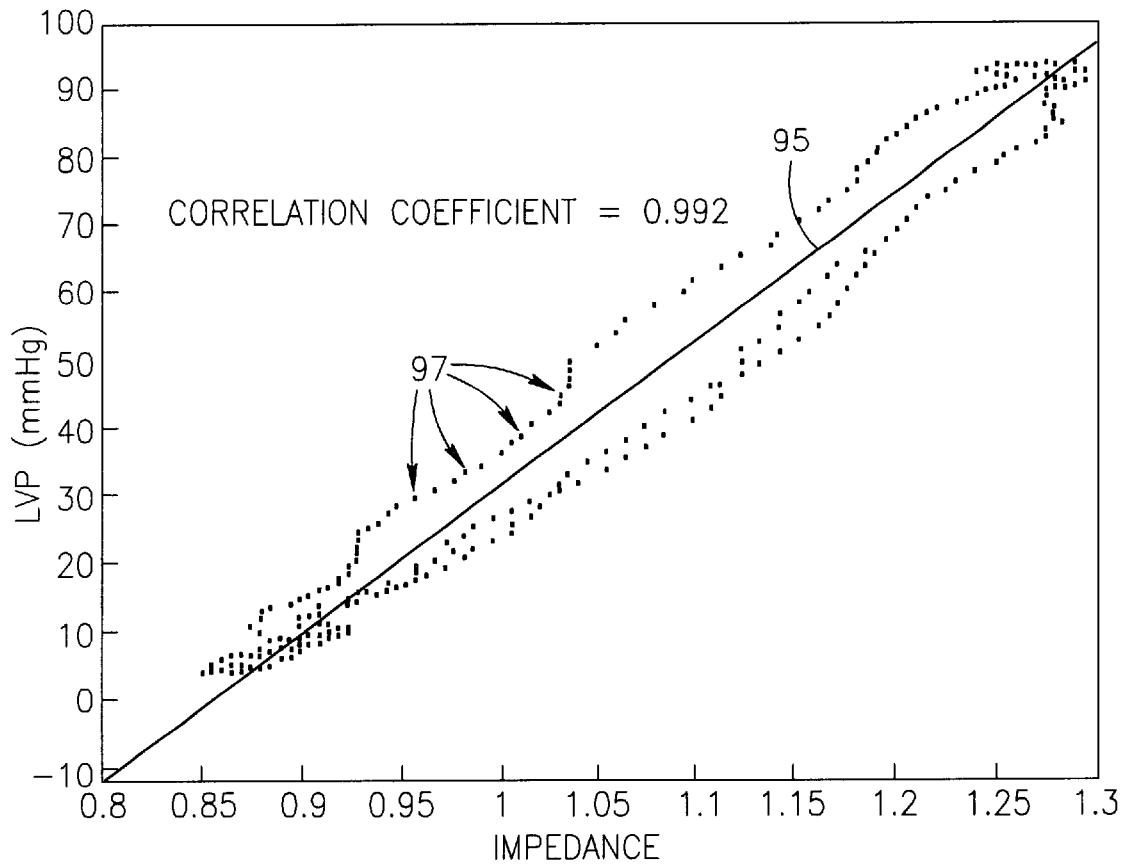
FIG. 6 is a schematic graph illustrating the data used to compute the correlation coefficient between the LVP and the impedance signal taken from a part of the experiment illustrated in FIGS. 5A–5D.

Reference is now made to FIG. 6 which is a schematic graph illustrating the data used to compute the correlation coefficient taken from another part of the experiment illustrated in FIGS. 5A–5D. The horizontal axis of FIG. 6 represents the LVP amplitude values in millimeters Hg. And the vertical axis of FIG. 6 represents the corresponding GCV impedance amplitude values in arbitrary units. The points 97 represent the data set points and the straight line 95 represents the curve fit to the points 97 using a linear regression curve fitting program. The correlation coefficient computed is r=0.992

This high correlation coefficient was typical to the experiment and similar values of r were found for data taken from other parts of the experiment.

Typically, as can be seen in FIGS. 5A–5D, the GCV impedance signal 92 is not highly affected by myocardial electrical activity. It was also experimentally found that the GCV impedance signal was not significantly affected by postural or movement changes induced in the dog.

It is noted that, while the above experiment described in EXAMPLE 1 demonstrates the ability of the intra-vessel impedance method and apparatus of the present invention to provide an impedance signal highly correlated to the cardiac left ventricular pressure, the methods and devices of intra-vessel impedance measurement may also be adapted for measuring an intra-vessel impedance within other blood vessels of other body organs or parts of the body, such as, but not limited to blood vessels mechanically coupled to the heart, the lungs, the uterus, the urinary bladder, a part of the gastrointestinal tract, the brain, the spinal cord and the intra-thoracic cavity. Such intra-vessel impedance signals may be correlated to mechanical properties of those organs or parts of the body, such as, but not limited to, the left ventricular pressure or the right ventricular pressure of the heart, the local or non-local mechanical contraction of the heart or of a portion thereof, the heart rate, the intra-uterine pressure, the contraction of the uterus or of a portion thereof, the pressure within the urinary bladder, local or non-local urinary bladder contractions, the intra-pulmonary pressure, the intra thoracic pressure, and the motility or contraction of a part of the gastrointestinal tract such as for example, the esophagus, the stomach, the small intestine, the large intestine or portions thereof.

It will be appreciated by those skilled in the art that, using the impedance methods and devices of the present invention to determine such mechanical properties or physiological parameters of the organs or body parts disclosed hereinabove or of other organs or body part may be applied to many useful applications, including, but not limited to, the use of such determined parameters or mechanical properties in various forms of rate adaptive pacemakers and metabolic demand pacemakers, the computing of a plurality of other useful parameters from the determined parameters, such as the rate of change of the LVP, the determination of the heart rate, methods and devices for distinguishing between ventricular fibrillation and ventricular tachicardia in implantable and non-implantable defibrillators or pacemakers including defibrillators, the measurement of pulmonary pressure for detection or prevention of pulmonary edema, the monitoring of uterine pressure or contractions for diagnostic purposes and in devices for modulating uterine contractility, the monitoring of gastrointestinal motility or contractions for diagnostic purposes and in devices for modulating intestinal contractions or motility contractility, the monitoring of urinary bladder pressure or contractions for diagnostic purposes and in devices for modulating urinary bladder contractions or motility contractility, and in many other different applications.

Moreover, the particular disclosed example of using the impedance determining methods and sensors and devices of the present invention for determining the left ventricular pressure may have important application. For example, one problem encountered in diagnostic and therapeutic cardiac devices using electrical sensing, is that it is difficult to reliably distinguish between ventricular tachicardia (VT) and ventricular fibrillation (VF) in a heart using a single electrical sensing electrode. In contrast, the impedance determining method and apparatus of the present invention provide a simple, reliable and practical method and device for differentiating VF from VT in a patient and for detecting, diagnosing and treating VF based on the diagnosing thereof. The method is based on the fact that in a case of VT, the LVP correlated impedance signal of the present invention will typically display a higher than normal rate of left ventricular pressure pulsations with a reduced pressure peak amplitude. In direct contrast, in a case of VF, the LVP correlated impedance signal of the present invention will typically display a drastic reduction of the pressure pulses characterized by a total or an almost total abolishing of the pressure wave pulsation in which the peak LVP pulsation amplitude is reduced to levels close to baseline levels.

Thus, devices such as, but not limited to pacemakers or automatic internal cardiac defibrillator (AICD) devices may be equipped with the impedance sensor and the impedance determining unit of the present invention and use them as disclosed hereinabove to monitor the LVP related impedance signal. Such a device may detect a suspected VF based on the simultaneous detection of increased heart rate sensed by an electrical sense electrode, and a flattening of the pulsatile LVP correlated impedance signal peak amplitude below a specified threshold level. Upon detection of such a suspected VF, the device may apply defibrillation pulses or other types of defibrillating therapy to the heart of the patient. Such a device may have the advantage of increasing the reliability in VF detection without adding additional leads electrodes or sensors to the device, since the impedance electrodes may be included in a pacing lead or the impedance may be measured by using existing electrodes which are also used for such purposes of sensing or pacing in the pacemaker part of the device.

Another possible application of the LVP correlated impedance measurement method and devices of the present invention is related to the diagnosis and possibly the treatment of cardiac electro-mechanical disassociation (EMD). EMD is a phenomenon in which the myocardial electrical activation is decoupled from the mechanical activation of the myocardium. For example, EMD may occur in patients defined as Heart Failure class 4 patients, in accordance with the New York Heart Association (NYHA) classification. In such patients, defibrillation therapy such as the delivery in defibrillating current pulses to the heart using of external or internal defibrillating electrodes, may result in restoration of the cardiac rhythmic electrical activity without the restoration of the cardiac mechanical contractility which is normally coupled to the cardiac electrical activity. This creates a serious problem, since based on the hearts electrical activity detected by electrical sensing methods such as ECG recording or intra-cardiac electrical sensing, the patient's heart seems to be functioning normally. Such a patient may therefore be diagnosed as normal while actually the patient is in a severe, life threatening condition since without mechanical cardiac contractility, no blood pumping occurs.

The LVP correlated impedance signal of the present invention may therefore be applied for detecting EMD in such patients or in other patients. When EMD occurs in a patient, the LVP correlated signal will show an immediate cessation or disappearing of the rhythmic variation in LVP. The impedance signal will drop to the baseline or close to the baseline. When this LVP ceases to exhibit pulsatile variations but the rhythmic electrical activity of the heart is concomitantly sensed by an electrical sense electrode, the device may diagnose a suspected EMD, and may also (optionally) initiate the delivery of EMD therapeutic measures.

Such an EMD detecting device may be used alone for diagnostic purposes, or as an integrated part of a pacemaker, a defibrillating device such as an AICD, a cardiac contractility modulating device or any combination thereof.

Such methods and devices for detecting and treating EMD in cardiac patients may have the advantage of reliably solving the difficulty of diagnosing EMD without adding complicated circuits or leads or additional sensors to the devices. As disclosed hereinabove, the intra-vessel impedance sensing may be performed using the same pair of electrodes which is also simultaneously usable for local electrogram sensing and may also be used for pacing (in the LV). This has the advantage of simplifying the devices design and ease of implantation.

Finally, it is noted that the impedance sensors and impedance determining circuits of the present invention and any devices which include them may be used for acute implantation in a patient for short term patient monitoring and treatment such as for temporary use in intensive care hospitalized patient's. Alternatively, the impedance sensors and impedance determining circuits of the present invention and any devices which include them may be constructed or used as implantable devices for chronic use such as, but not limited to, pacemakers, rate adaptive pacemakers, defibrillators, AICD devices or the like.

Devices for monitoring, and/or diagnosing and/or treating any of the other organs and body parts other than the heart may also be adapted for acute and for chronic implantation in patients.

It will be appreciated that the preferred embodiments disclosed hereinabove and illustrated in the drawings are given by way of example and that many variations and modifications of the present invention may be made which are within the scope and spirit of the present invention.

What is claimed is:

1. A method for determining the left ventricular pressure of a heart, the method comprising the steps of:

positioning an impedance sensor within a coronary blood vessel of said heart, said impedance sensor has at least two electrodes disposed within said coronary blood vessel; and determining the electrical impedance between said at least two electrodes to obtain an impedance signal said impedance signal is correlated with said left ventricular pressure, the correlation coefficient of said impedance signal and sad left ventricular pressure has a value higher than 0.8.

2. The method according to claim 1 further including the step of processing said impedance signal to determine said left ventricular pressure.

3. A method for determining the left ventricular pressure of a heart, the method comprising the steps of:

positioning an impedance sensor within a coronary blood vessel of said heart, said impedance sensor has at least two electrodes disposed within said coronary blood vessel; and determining the electrical impedance between said at least two electrodes to obtain an impedance signal said impedance signal is correlated with said left ventricular pressure, the correlation coefficient of said impedance signal and sad left ventricular pressure has a value higher than 0.95.

4. The method according to claim 3 further including the step of processing said impedance signal to determine said left ventricular pressure.

5. A method for determining the left ventricular pressure of a heart, the method comprising the steps of:

positioning an impedance sensor within a coronary blood vessel of said heart, said impedance sensor has at least two electrodes disposed within said coronary blood vessel; and determining the electrical impedance between said at least two electrodes to obtain an impedance signal correlated with said left ventricular pressure, said impedance signal is substantially unaffected by postural changes.

6. The method according to claim 5 further including the step of processing said impedance signal to determine said left ventricular pressure.

7. A method for sensing a signal correlated with the left ventricular pressure of a heart, the method comprising the steps of:

positioning an impedance sensor within a coronary blood vessel of said heart, said impedance sensor has at least two electrodes disposed within said coronary blood vessel; and determining the electrical impedance between said at least two electrodes to obtain an impedance signal correlated with said left ventricular pressure the correlation coefficient of said impedance signal and said left ventricular pressure has a value higher than 0.8.

8. A method for sensing a signal correlated with the left ventricular pressure of a heart, the method comprising the steps of:

positioning an impedance sensor within a coronary blood vessel of said heart, said impedance sensor has at least two electrodes disposed within said coronary blood vessel; and determining the electrical impedance between said at least two electrodes to obtain an impedance signal correlated with said left ventricular pressure the correlation coefficient of said impedance signal and said left ventricular pressure has a value higher than 0.95.

9. A method for sensing a signal correlated with the left ventricular pressure of a heart, the method comprising the steps of:

positioning an impedance sensor within a coronary blood vessel of said heart, said impedance sensor has at least two electrodes disposed within said coronary blood vessel; and determining the electrical impedance between said at least two electrodes to obtain an impedance signal correlated with said left ventricular pressure, said impedance signal is substantially unaffected by postural changes.

* * * * *

UNITED STATES PATENT AND TRADEMARK OFFICE
CERTIFICATE OF CORRECTION

PATENT NO.    : 6,360,123 B1
DATED         : March 19, 2002
INVENTOR(S)   : Yoav Kimchi It is certified that error appears in the above-identified patent and that said Letters Patent is hereby corrected as shown below:

<u>Column 16,</u>
Lines 32 and 47, the word "sad" should be replaced with the word -- said --.

Signed and Sealed this

Twenty-ninth Day of July, 2003

JAMES E. ROGAN
*Director of the United States Patent and Trademark Office*